(12) United States Patent
Koller et al.

(10) Patent No.: US 11,346,827 B2
(45) Date of Patent: May 31, 2022

(54) MEASURING CONCENTRATIONS OF A TARGET GAS

(71) Applicant: SENSIRION AG, Stäfa (CH)

(72) Inventors: Marcel Koller, Stäfa (CH); Felix Hoehne, Stäfa (CH)

(73) Assignee: SENSIRION AG, Stäfa (CH)

( * ) Notice: Subject to any disclaimer, the term of this patent is extended or adjusted under 35 U.S.C. 154(b) by 282 days.

(21) Appl. No.: 16/616,877

(22) PCT Filed: Jul. 27, 2018

(86) PCT No.: PCT/EP2018/070502
§ 371 (c)(1),
(2) Date: Nov. 25, 2019

(87) PCT Pub. No.: WO2018/220238
PCT Pub. Date: Dec. 6, 2018

(65) Prior Publication Data
US 2021/0278383 A1    Sep. 9, 2021

(30) Foreign Application Priority Data
Aug. 14, 2017   (EP) .................... 17186147

(51) Int. Cl.
*G01N 33/00* (2006.01)
*G01N 27/04* (2006.01)
*G01N 27/403* (2006.01)

(52) U.S. Cl.
CPC ......... *G01N 33/0016* (2013.01); *G01N 27/04* (2013.01); *G01N 33/0047* (2013.01); *G01N 27/403* (2013.01)

(58) Field of Classification Search
CPC ............... G01N 33/0016; G01N 27/04; G01N 33/0047; G01N 27/403; G01N 33/0009;
(Continued)

(56) References Cited

U.S. PATENT DOCUMENTS 5,525,280 A    6/1996   Shukla et al.
6,499,354 B1  12/2002   Najafi et al.
(Continued)

FOREIGN PATENT DOCUMENTS

DE    102005008959 B4    8/2012
EP         2642289           9/2013
(Continued)

OTHER PUBLICATIONS

International Search Report and Written Opinion dated Sep. 24, 2018, PCT Patent Application No. PCT/EP2018/070502, filed Jul. 27, 2018, European Patent Office, 13 pages.
(Continued)

*Primary Examiner* — Robert R Raevis
(74) *Attorney, Agent, or Firm* — Mannava & Kang, P.C.

(57) ABSTRACT

An electronic device comprises a gas sensor sensitive to a target gas and arranged inside a housing of the electronic device or attached thereto, to detect a concentration of the target gas in an environment of the electronic device. A processing unit is provided and configured to determine a concentration of the target gas outgassed from one or more components of the housing or inside the housing dependent on one or more first measurement results supplied by the gas sensor in response to one or more first measurements, and to determine the environmental target gas concentration dependent on the determined outgassed target gas concentration and dependent on a second measurement result ($R_{OM}$) supplied by the gas sensor in response to a second measurement (OM). Outgassing is understood as the release of chemical substances from the one or more components.

19 Claims, 2 Drawing Sheets

(58) Field of Classification Search
CPC ....... G01N 33/0006; G01N 2021/3545; G01N 33/0014; G01N 33/0059
USPC .......... 73/1.02, 1.06, 31.05, 31.06; 324/669, 324/670, 684, 685, 693, 717, 720, 721, 324/601, 130; 338/13, 34
See application file for complete search history.

(56) References Cited

U.S. PATENT DOCUMENTS

| | | |
|---|---|---|
| 7,704,774 B2 | 4/2010 | Mayer et al. |
| 9,958,349 B2 | 5/2018 | Schumm et al. |
| 2008/0236292 A1 | 10/2008 | Reijs |
| 2009/0166827 A1 | 7/2009 | Foster et al. |
| 2010/0207217 A1 | 8/2010 | Zuniga-Ortiz et al. |
| 2013/0264755 A1 | 10/2013 | Eskridge |
| 2013/0276544 A1 | 10/2013 | Potasek et al. |
| 2015/0122041 A1 | 5/2015 | Lin et al. |
| 2017/0184558 A1 | 6/2017 | Berndt et al. |

FOREIGN PATENT DOCUMENTS

| | | |
|---|---|---|
| EP | 2765410 | 8/2014 |
| EP | 2246292 B1 | 11/2014 |
| EP | 3203229 | 8/2017 |

OTHER PUBLICATIONS

Roger Allan, "MEMS Inertial Sensors Push Size, Performance Limits For Next-Gen Mobile Devices", Electronic Design, Apr. 13, 2010, 15 pages. https://www.electronicdesign.com/technologies/components/article/21790914/mems-inertial-sensors-push-size-performance-limits-for-nextgen-mobile-devices.

Roger Allan, "Ever-Shrinking ICs Turn To Exotic Packaging Methods", Electronic Design, Jan. 14, 2009, 13 pages. http://electronicdesign.com/interconnects/ever-shrinking-ics-turn-exotic-packaging-methods.

MEASURING CONCENTRATIONS OF A TARGET GAS

TECHNICAL FIELD

The present invention relates to an electronic device and to a method for determining a concentration of a target gas in an environment of an electronic device.

BACKGROUND ART

Today's gas sensors may be mounted in or to electronic devices, the latter typically comprising a printed circuit board and/or a housing.

While a gas sensor may be arranged in or at such electronic device for measuring an ambient concentration of a target gas the gas sensor is sensitive to, it was found that the electronic device itself, e.g. its housing, its circuit board or other components inside the housing, may outgas the target gas, too, which portion of the target gas outgassed by the device falsifies the measurement of the concentration of the target gas in the ambient.

Patent application US 2017/184558 A1 discloses a method for operating a test station for portable gas-measuring devices. The gas-measuring device is arranged in fluid-communication with the test station via at least one interface. A flow time is set, during which the test gas is fed and a waiting time is set, during which no test gas is fed. After an end of the feed of the at least one test gas results of the test are analyzed. The test station is configured for feeding at least one test gas to the interface. The test station for portable gas-measuring devices has at least one interface for the fluid-communicating arrangement of the gas-measuring device, and wherein the test station is configured for feeding at least one test gas to the interface.

Patent application EP 3203229 A2 shows a gas sensor comprising a sensing element of a material including metal oxide and being sensitive to a target gas and to a recalibration gas different from the target gas. For recalibrating the gas sensor, a resistance of the sensing element is measured as an updated recalibration gas baseline resistance in a recalibration environment showing a recalibration gas baseline concentration.

Patent application EP 2765410 A1 provides a gas sensor package comprising a gas sensor chip with a layer sensitive to a gas, and with a heater for heating the sensitive layer. Contact pads are provided for electrically contacting the gas sensor package and a die pad is provided for mounting the gas sensor chip to. Electrical connections connect the gas sensor chip and the contact pads. A molding compound at least partially encloses the gas sensor chip. An opening in the molding compound provides access to the sensitive layer of the gas sensor chip. One of the contact pads serves as a pin for supplying electrical current to the heater of the gas sensor chip.

Patent application EP 2642289 A1 discloses a method for operating a portable electronic device wherein a recharge process for recharging a rechargeable energy storage of the portable electronic device is detected. A heater is activated for heating a sensitive layer of a chemical sensor contained in the portable electronic device subject to the detection of the recharge process.

DISCLOSURE OF THE INVENTION

The problem to be solved by the present invention is therefore to provide an electronic device and a method for determining a concentration of a target gas in an environment of an electronic device in which an impact of the portion of the target gas produced by the device itself is reduced.

This problem is solved by a method according to the features of claim 1, and by an electronic device according to the features of claim 13.

The electronic device comprises a gas sensor sensitive to a target gas and arranged in or at the electronic device to detect a concentration of the target gas in an environment of the electronic device.

The electronic device may be a portable electronic device such as a mobile phone, and in particular a smart phone, a handheld computer, an electronic reader, a tablet computer, a game controller, a pointing device, a photo or a video camera, or a computer peripheral. In a different embodiment, the electronic device is a stationary device such as a chemical nose mounted to a wall of a room the atmosphere of which room is to be investigated. Accordingly, a user of the electronic device may learn about chemical substances and compositions present in the device surroundings, i.e. in the gas of the environment of the electronic device. The outcome of such measurements may be used, transmitted or else further be analysed.

The gas sensor may comprise a gas sensing layer which is sensitive to a target gas. Hence, one or more chemical compounds or analytes present in a gas, also referred to as target gas, can be detected by the gas sensor. In one embodiment, the target gas may be or contain Volatile Organic Compounds (VOCs), or individual compounds thereof, such as carbon monoxide, nitrogen dioxide, methane, ammonia or hydrogen sulphide. Specifically, the gas sensor is embodied and arranged for detecting one or more chemical substances in a gas, and specifically in the air surrounding the electronic device. Hence, in a sample application it may be of interest to identify if such air contains certain analytes the gas sensor is prone to. A specific application may include the detection of toxic gases.

In one embodiment, the sensing layer may contain a metal-oxide material, and in particular a semiconducting metal oxide material. Such metal oxide material may include one or more of tin oxide, zinc oxide, titanium oxide, tungsten oxide, indium oxide and gallium oxide. Such metal oxides may be used for the detection of analytes such as VOCs including one or more of carbon monoxide, nitrogen dioxide, methane, ammonia or hydrogen sulphide. Metal-oxide gas sensors are based on the concept that the target gas interacts with the metal oxide layer at elevated temperatures of the sensing layer in the range of more than 100° Celsius, and specifically between 250° C. and 350° Celsius. As a result of a catalytic reaction, the conductivity of the sensing layer may change which change can be measured. Hence, such chemical sensors are also denoted as high temperature chemoresistors for the reason that a chemical property of the analyte is converted into an electrical resistance at high temperatures of the sensitive layer. Accordingly, the sensing layer preferably is heated by the heater prior to taking a reading, and preferably during taking a reading for elevating a temperature of the sensing layer to a temperature sufficient for having a catalytic reaction between the analyte/s of the target gas and the sensing layer to take place at a sufficient rate and as a result, for example, for having an electrical conductivity of the sensing layer modified. In case the gas sensor is sensitive to multiple different analytes the gas sensor may be embodied as a sensor array. In such sensor array, each sensor cell may provide a different sensor material and/or may be operated under different parameters.

However, gas sensors other than chemoresistors can be used, such as electro-chemical gas sensors.

The gas sensor preferably is embodied as gas sensor chip including a semiconductor substrate with the sensing layer arranged on or in the chip. Preferably a recess is manufactured into the semiconductor substrate generating a thin membrane the sensing layer is arranged on or in, as well as a heater for heating the sensing layer. The membrane is also denoted as micro-hotplate for the reason that such membrane to a large extent constitutes a thermally insulating structure. Hence, any heat generated by the heater affects the sensing layer as desired but does not leak into the bulk.

The gas sensor is arranged inside a housing of the electronic device, or is attached thereto. An opening may be provided in the housing for exposing the gas sensor to the target gas from the environment of the electronic device. Preferably, a cavity is formed in the housing and the gas sensor is arranged in the cavity. The cavity may connect to the environment via e.g. such opening in the housing. Such arrangement mechanically protects the gas sensor. In one embodiment, the gas sensor may be arranged on and electrically connected to a carrier such as a printed circuit board (PCB), which carrier may also be considered as a component contributing to the forming of the housing or the cavity. In another embodiment, the electronic device may comprise more than one carrier such as a PCB, the carriers being components of or inside the housing or the cavity. The gas sensor may alternatively be arranged on one of these latter carriers.

It was found that components of the housing or inside the housing e.g. made from plastics, rubber or including adhesives may outgas, and in particular may outgas the target gas the gas sensor is sensitive to. In this context, outgassing is understood as the release of chemical substances from the subject tangible component. In case of a cavity, components contributing to and/or forming the cavity may outgas, in particular when containing one or more of plastics, rubber, or adhesives. Also components inside the cavity may outgas, in particular a battery, other electronic components, a PCB, or a coating of the PCB, if present. In case of outgassing, and in particular of outgassing the target gas the gas sensor is sensitive to, and assuming that the outgassed target gas reaches the gas sensor, a measurement result of the gas sensor is impacted given that the gas sensor is supposed to only supply the concentration of the target gas in the environment of the electronic device without any contribution of the device originating target gas concentration, i.e. the outgassed target gas concentration. However, what is actually measured by the gas sensor is an accumulation of the environment originating target gas concentration and of the device originating target gas concentration originating from outgassing processes of the electronic device itself. Whenever the gas sensor takes a measurement of a concentration of the target gas, the measurement result typically is composed of these two different concentration portions originating from two different sources, i.e. the environment and the device.

Accordingly, a processing unit is provided and configured to first determine a concentration of the target gas originating from the electronic device. This determination may be made dependent on a result of one or more first measurements supplied by the gas sensor and referred to as first measurement results in the following. The first measurements are also referred to as preparatory measurements given that these measurements rather aim at identifying the target gas concentration resulting from the device's outgassing activities than at identifying the target gas concentration of the environment.

Once the concentration of the target gas originating from the electronic device—also referred to as device originating target gas concentration—is determined, operational measurements can be started with the aim of determining the concentration of the target gas in the environment of the electronic device—also referred to as environmental target gas concentration. In such second measurement, the gas sensor supplies a measurement result referred to as second measurement result. However, as indicated above, the second measurement result again is composed from two target gas concentrations, i.e. the environmental one and the device originating one. Accordingly, the environmental target gas concentration is determined dependent on the second measurement result and dependent on the device originating target gas concentration.

According to the method aspect of the present invention, the concentration of the target gas in an environment of an electronic device is determined by means of the gas sensor sensitive to the target gas and arranged in or at the electronic device, by executing the steps: Conducting one or more first measurements by the gas sensor and supplying one or more first measurement results; determining the concentration of the target gas originating from the electronic device dependent on the one or more first measurement results; conducting a second measurement by the gas sensor and supplying a second measurement result; and determining the environmental target gas concentration dependent on the determined device originating target gas concentration and dependent on the second measurement result.

According to a further aspect of the present invention, a computer program element is provided, and in particular a computer program medium is provided, comprising computer program code means for implementing a method according to any one of the preceding and subsequent embodiments of the method when being executed on a processing unit.

As a result, a concentration of the target gas stemming from the environment only is determined, i.e. without contributions of the target gas stemming from outgassing processes of the device itself. Accordingly, the final output value represents the environmental target gas concentration only rather than an accumulation of the environmental and a device originating target gas concentration. The elimination of the device originating target gas concentration is performed by using results of antecedent one or more first measurements.

The device originating target gas concentration, as was found by the inventors, may vary subject to the temperature of the components responsible for the outgassing on the one hand, and on the other hand may also vary over time. As to the temperature dependency, it was found that the higher the temperature of the relevant components are, the higher the device originating target gas concentration is. As to the time dependency, it was found that typically in the long term the older the components become, the lower the device originating target gas concentration becomes. However, temporary increases owed to mechanical stress can also be observed.

In order to address the temperature dependency, according to an embodiment of the present invention, multiple first measurements are conducted at different temperatures resulting in temperature dependent first measurement results. The relevant temperature preferably is the temperature of the components outgassing into the volume the gas sensor takes its measurements from. In one approach, this temperature may be approximated by the temperature of the electronic device measured e.g. by a temperature sensor arranged in or at the housing of the electronic device. In a different variant, a temperature sensor is provided in the cavity if any, in order to specifically measure the temperature at the location of gas measurement, and hence of the gas sensor, which may be a viable approximation to the temperature of the components outgassing. For example, a temperature sensor may be embodied in the same chip together with the gas sensor, and be arranged in the cavity if any.

It is preferred, that device originating target gas concentrations are derived for different temperatures by making use of the first measurement results. The relevant temperature may be measured by a temperature sensor as explained above and at least may temporarily be stored in the device. Once the device originating target gas concentrations are determined by the processing unit, these values preferably are stored in combination with the corresponding temperatures the first measurements were taken at.

In an embodiment, a characteristic of device originating target gas concentrations over temperature is derived from the temperature dependent first measurement results and from the associate measured temperatures, in particular by interpolation or by extrapolation. E.g. two first measurement results may be provided by the gas sensor for two different temperatures. While these two first measurement results may include an environmental target gas concentration offset, which may be assumed as constant during the first measurements, a slope of the characteristic may be determined from a difference between the two first measurement results divided by a difference between the two associate measured temperatures. Having determined the slope, the environmental target gas concentration offset is determined dependent on the slope and dependent on at least one of the two first measurement results and the associate measured temperature. In this sense, the characteristic of device originating target gas concentrations over temperature may be determined and be represented by a formula with the temperature serving as input. This characteristic preferably is used to finally determine the environmental target gas concentration.

When the device originating target gas concentrations are determined and stored in combination with the associate temperatures, or are stored as look up table, or as formula with a dependency from temperature, it is preferred that when conducting a subsequent operational measurement for determining the environmental target gas concentration, the temperature is measured, too, in combination with the target gas measurement. For this purpose, it is preferred to use the same temperature sensor that was used when determining the device originating target gas concentrations over temperature. "In combination with the target gas measurement" in this context means that the temperature may be measured simultaneously with the target gas measurement, or soon before or soon after, such it can be expected that the temperature at the time of the gas measurement and the temperature at the time of the temperature measurement do not deviate significantly, e.g. by a maximum of ten percent, since it is of interest to capture the temperature that dominates during the target gas measurement. The same is true for the temperature measurements in combination with the first measurements.

Once the current temperature is measured, the corresponding device originating target gas concentration value can be looked up or can be calculated, such that in the following the environmental target gas concentration can be determined dependent on the second measurement result and dependent on the device originating target gas concentration as determined for the measured temperature.

As to the point in time when to start conducting the multiple first measurements for determining the temperature dependent device originating target gas concentrations, various temperatures should be covered by the first measurements. While one may envisage to use the heater of the gas sensor in case of a chemoresistive gas sensor for generating the various temperatures, it is preferred to use other heat sources given that the above heater may be thermally isolated on a membrane of the gas sensor as laid out above. Relevant heat sources may be represented e.g. by electrical components, and in particular by electrical components thermally coupled to the outgassing components. Electrical components that radiate heat and may be provided anyway in an electronic device may e.g. be the processing unit, a battery, a display, a GPS receiver, or an RF transceiver. One of or any combination of these electrical components may radiate heat when being active/activated, and may trigger the first measurements in response to an activation, for example. The subject electrical component may be activated on purpose for generating a rising temperature for the first measurements. However, in an alternative, the first measurements may rather be triggered when the electrical component is detected to be in a state promising varying temperatures, e.g. in response to being activated. The activation or a rise in the performance of an electrical component in turn may be detected in many different ways: First, a temperature sensor arranged in or close to the electrical component, or alternatively, arranged in or close to the outgassing component, or arranged in or close to the gas sensor may indicate such rise in temperature triggering the first measurements. In an alternative or in addition, software/flags may indicate the activation of such electrical component. And/or, measurements of electrical sensors, such as a sensor measuring a current etc. may be used. And/or mechanical sensors such as a plug detector recognizing the plug-in of a charging cable may be used.

Specifically, the first measurements may be triggered in response to a recharge process for recharging the battery of the device being detected, or may be triggered in response to the CPU load exceeding a given level, or in response the display intensity exceeding a given value, etc.

A heating for provoking outgassing may also be generated by external heat sources such as sunlight or a human body.

On the other hand, it may be preferred to conduct the first measurements at a period in time when the environmental target gas concentration is expected not or only slightly to change. This facilitates the determination of the device originating target gas concentration. Accordingly, it may be preferred that the first measurements are conducted e.g. at a predetermined point in time, in particular wherein the predetermined point in time is defined as a specific time of day, such as a specific time at night wherein e.g. it can be expected that e.g. the room the electronic device is in is not exposed to changes e.g. to changes in the VOC concentration in view of reduced activities in such room at night.

In a different embodiment, the device originating target gas concentration may also be determined by using statistics, e.g. by generating a plot between concentration and temperature values and estimating the device originating target gas concentration therefrom.

In order to address a varying device originating target gas concentration over time, e.g. due to the aging of the materials outgassing, it is preferred to repeat the one or more first measurements. The trigger for preforming such first measurements results resulting in updated first measurement results may be a constant or a dynamic interval in time, e.g. every three months, years, or similar. Once these first measurement are taken anew, an updated device originating target gas concentration can be determined dependent on the one or more updated first measurement results. Any determination of an environmental target gas concentration after the determination of the updated device originating target gas concentration preferably is based on the latter, and of course is based on the second measurement result then supplied by the gas sensor.

Preferably, the environmental target gas concentration $c_{amb}$ is determined according to:

$$c_{amb} = \left(\frac{R_{OM}}{R_B}\right)^{\frac{1}{n}} * c_B - c_B$$

wherein:
$c_B$ is the device originating target gas concentration;
$R_{OM}$ is the second measurement result;
$R_B$ is the first measurement result corresponding to the device originating target gas concentration $c_B$;
n is a sensitivity of the gas sensor to the target gas; it may be derived during production of the gas sensor.

Preferably, the processing unit performing the determinations and/or calculations may be arranged on a common carrier together with the gas sensor, or on a different carrier. In one embodiment, the processing unit may be integrated in the same chip as the gas sensing layer, and hence is monolithically integrated together with the gas sensor.

In a preferred embodiment, the sensing layer may be heated from time to time even outside gas measurements taking place, which heating is also referred to as reconditioning heating. Such measures may be taken for reconditioning a sensing layer that was found not to be operated at elevated temperatures for quite some time which may result in an offset drift. This offset drift may be reversed by activating the heater and by heating the sensitive layer for a sufficient period of time. However, the present ideas rather refer to the problem of noticing and eliminating target gas concentrations in the measurement results that do not stem from the environment but from the device itself.

Other advantageous embodiments are listed in the dependent claims as well as in the description below.

The described embodiments similarly pertain to the apparatus, the method and the computer program element. Synergetic effects may arise from different combinations of the embodiments although they might not be described in detail.

BRIEF DESCRIPTION OF THE DRAWINGS

The embodiments defined above and further aspects, features and advantages of the present invention can also be derived from the examples of embodiments to be described hereinafter and are explained with reference to the drawings. In the drawings the figures illustrate in FIG. 1 a schematic electronic device according to an embodiment of the present invention, FIG. 2 a diagram showing various charts thereby illustrating a method according to an embodiment of the present invention, FIG. 3 sample concentration characteristics used for introducing a method according to an embodiment of the present invention, and FIG. 4 a flow chart representing a method for operating a portable electronic device according to an embodiment of the present invention.

MODES FOR CARRYING OUT THE INVENTION

Figure 1:
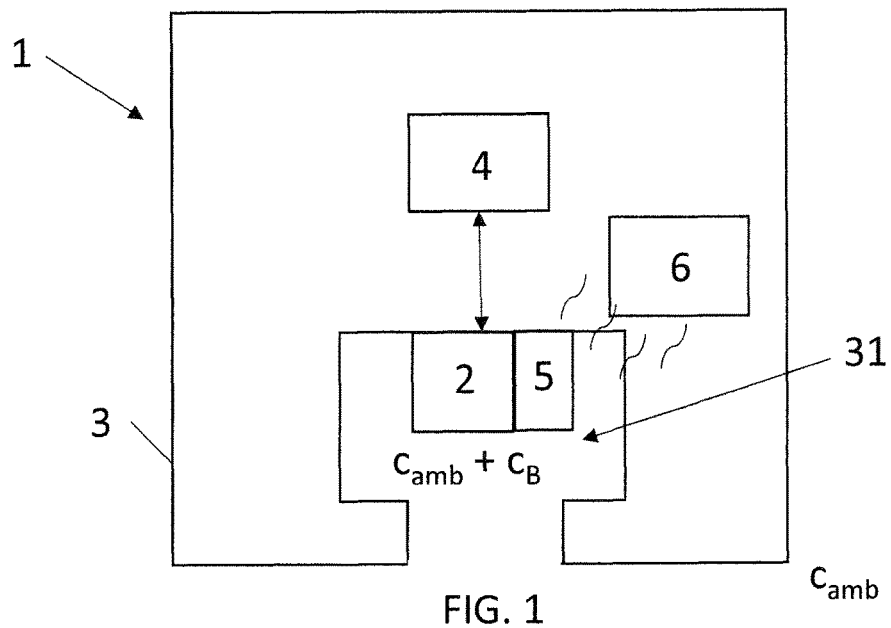

Same or similar elements are referred to by the same reference numerals across all Figures.

FIG. 1 illustrates an electronic device 1 according to an embodiment of the present invention. The electronic device 1 is only schematically illustrated, does not scale, and may be embodied in many different ways. The electronic device 1 comprises a housing 3 and a cavity 31 in the housing 3. A gas sensor 2 is arranged inside the cavity 31, in particular in view of mechanical protection. A temperature sensor 5 is arranged in the cavity 31, e.g. next to the gas sensor 2.

A processing unit 4 is comprised in the electronic device 1 and receives measurement results in form of signals from the gas sensor 2 and the temperature sensor 5. On the other hand, the processing unit 4 may control the gas sensor 2, and possibly the temperature sensor 5, e.g. by triggering a measurement of the gas sensor 2, in one embodiment including activating a heater of the gas sensor 2 prior to taking a measurement, in particular in case the gas sensor 2 is a metal oxide based chemoresistive gas sensor 2.

The electronic device 1 may include a battery 6, such as a rechargeable battery, for powering the functions of the electronic device 1, and specifically for powering the processing unit 4 and the gas sensor 2. As is indicated in FIG. 1, the battery 6 may be thermally coupled to the housing 3, and in particular to the cavity 31. In particular, upon recharging the battery 6 heat may be generated that heats up components of the housing 3, such as components building the cavity 31.

The gas sensor 2 and, if available, the temperature sensor 5, may be arranged on and electrically connected to a carrier such as a printed circuit board (PCB), which may also contribute to forming the cavity 31. Additionally there may be more carriers such as further PCBs. The processing unit 4 may be arranged on the same carrier, or on a different carrier. Other components of the housing 3 contributing to the cavity 31 may include one or more of: plastic parts of the housing, rubber parts e.g. for sealing purposes, adhesives. There may also be further electrical components inside the housing 3 and/or the PCB may be coated. The gas sensor 2 preferably is embodied as integrated gas sensor chip containing a semiconductor substrate, for example. In one embodiment, the processing unit 4 is integrated into the gas sensor chip. The temperature sensor 5 may be integrated into the same chip. In a different embodiment, the gas sensor 2, the temperature sensor 5 and the processing unit 4 may be embodied as discrete elements assembled e.g. on a common PCB.

The gas sensor 2 is arranged to measure a concentration $c_{amb}$ of a target gas in the environment, which may include one or more VOCs in one embodiment. As is illustrated in FIG. 1, the environmental target gas concentration $c_{amb}$ can be found in the environment of the electronic device 1. The environmental target gas concentration $c_{amb}$ diffuses into the cavity 31 and finally can be detected there by means of the gas sensor 2. However, components of the electronic device 1, such as the PCB, plastic parts of the housing, rubber and/or adhesive material may also outgas VOCs, i.e. the target gas to be detected by the gas sensor 2. Accordingly, a portion of the target gas inside the cavity 31 may not originate from the environment but from the electronic device itself.

Accordingly, what is actually measured by the gas sensor 2 is an accumulation of the environment originating target gas concentration $c_{amb}$ and of the device originating target gas concentration $c_B$. Whenever the gas sensor takes a measurement, the supplied measurement result typically is composed of two different concentration portions originating from the two different sources, i.e. the environment and the device.

Figure 2:
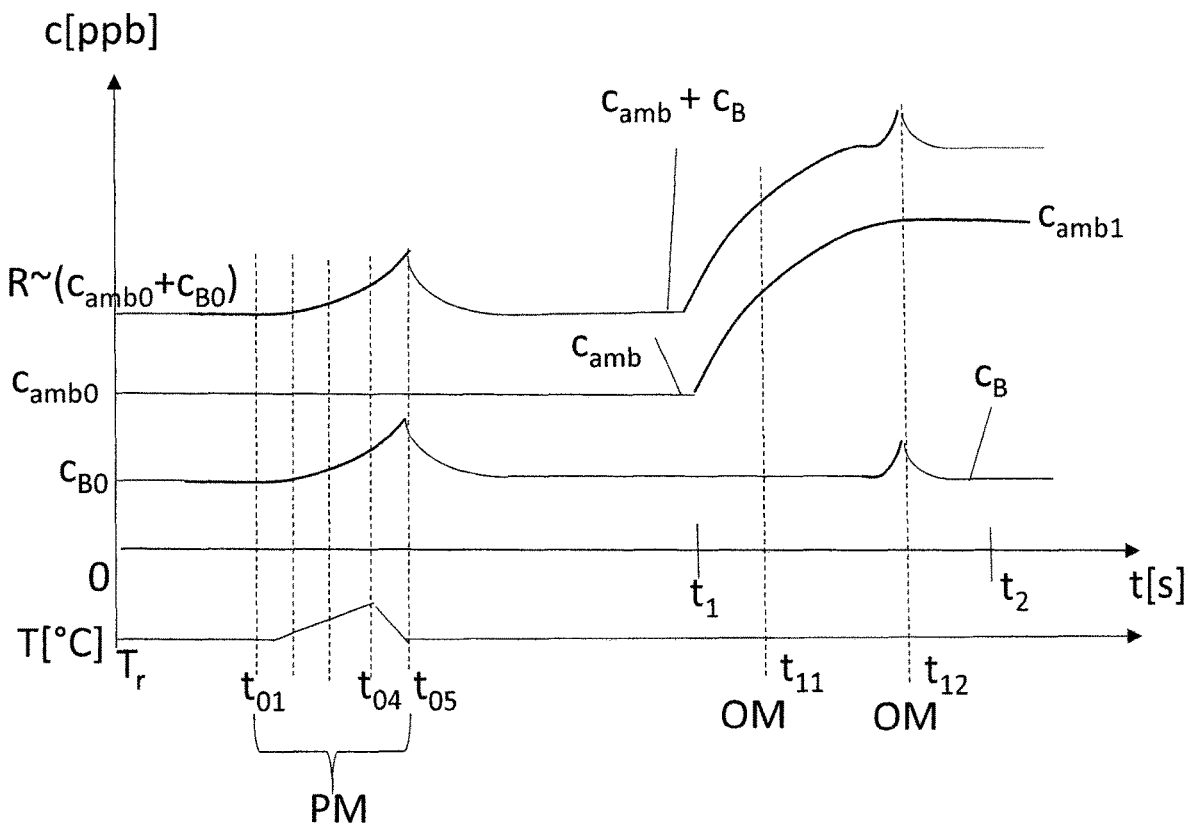

FIG. 2 shows a diagram of sample target gas concentrations over time supporting an understanding of the method according to an embodiment of the present invention.

The target gas concentration originating from the electronic device itself, also named the outgassed target gas concentration, is denoted as $c_B$. The target gas concentration of the environment is denoted as $c_{amb}$. In FIG. 2, the device originating target gas concentration $c_B$ is assumed to be a constant $c_{B0}$ over time t except for two peaks, one in the interval $0<t<t_1$, the other one in the interval $t_1<t<t_2$. The constant $c_{B0}$ is also referred to as baseline concentration $c_{B0}$ or background concentration $c_{B0}$. It is assumed that the rise in the device originating target gas concentration $c_B$ from constant $c_{B0}$ is caused by a rise in temperature of/in the electronic device. For example, it may be assumed that components of the device 1 defining a cavity are heated and cause a rise in the target gas released from these components. It is assumed, that at time $t=t_{01}$ the temperature T e.g. of the subject components that outgas into the cavity 31 ramps up, e.g. starting from room temperature $T_0$, and falls back to room temperature $T_r$ at time $t=t_{04}$ as is indicated in the temperature T over time t chart in FIG. 2. This causes the device originating target gas concentration $c_B$ to rise from constant $c_{B0}$ to a maximum at $t=t_{04}$ in view of the inertness of the system, and a subsequent fall down to constant $c_{B0}$ again.

The target gas concentration of the environment $c_{amb}$ is assumed to be constant $c_{amb0}$ over time t in interval $0<t<t_1$, and rises asymptotically in the interval $t_1<t<t_2$. Accordingly, a scenario is shown in which during the first interval $0<t<t_1$ the electronic device is maintained in an environment with a constant target gas concentration $c_{amb0}$ while in the second interval $t_1<t<t_2$ either the location of the electronic device remains as is but the target gas concentration in the same environment rises, or the electronic device changes location and is brought into a new environment with a different target gas concentration $c_{amb1}$. The upper graph shown in FIG. 2 represents the accumulated target gas concentration $c_{amb}+c_B$ that is measured by the gas sensor, e.g. the gas sensor 2 of FIG. 1. Accordingly, given that the gas sensor supplies measurement results R, it is assumed that the measurement results R are proportional to the sum of the two target gas concentrations:

$$R \sim (c_{amb}+c_B) \quad \text{(I)}$$

Within the first interval $0<t<t_1$, first measurements PM are taken by the gas sensor, and in particular five first measurements PM are taken at times $t_{01} \ldots t_{04}, t_{05}$ indicated by the dashed lines. These first measurements are also referred to as preparatory measurements given that their aim is to determine the target gas concentration $c_B$ originating from the device and not the environmental target gas concentration $c_{amb}$ that is determined in the subsequent operational measurement. For this reason, it is preferred to choose an interval in time for the first measurements PM in which the environmental target gas concentration $c_{amb}$ remains or is expected to be more or less constant, i.e. $c_{amb0}$ in the present example. In such scenario, device components exposed to heat and outgassing into the cavity cause the device originating target gas concentration $c_B$ to rise, and fall again after a drop in temperature, i.e. after a deactivation of the heat source.

Preferably, the first measurements PM are triggered by an indicator for a change or an expected change in temperature, and in particular for a rise of the relevant temperature T. For this reason, a temperature sensor such as the temperature sensor 5 of the electronic device 1 of FIG. 1 may measure the temperature T of the cavity 31. In case the temperature T rises, and preferably if such temperature rise exceeds a threshold, the first one of the first measurements PM is executed and finally provides a first measurement result R at $t=t_{01}$ $$R(t=t_{01};T=T_0) \sim c_{amb0}+c_{B0}.$$

In the same way further first measurements PM are conducted at subsequent times $t_{02}$, $t_{03}$, $t_{04}$, $t_{05}$, and the corresponding measurement results R(t,T) are recorded.

Figure 3:
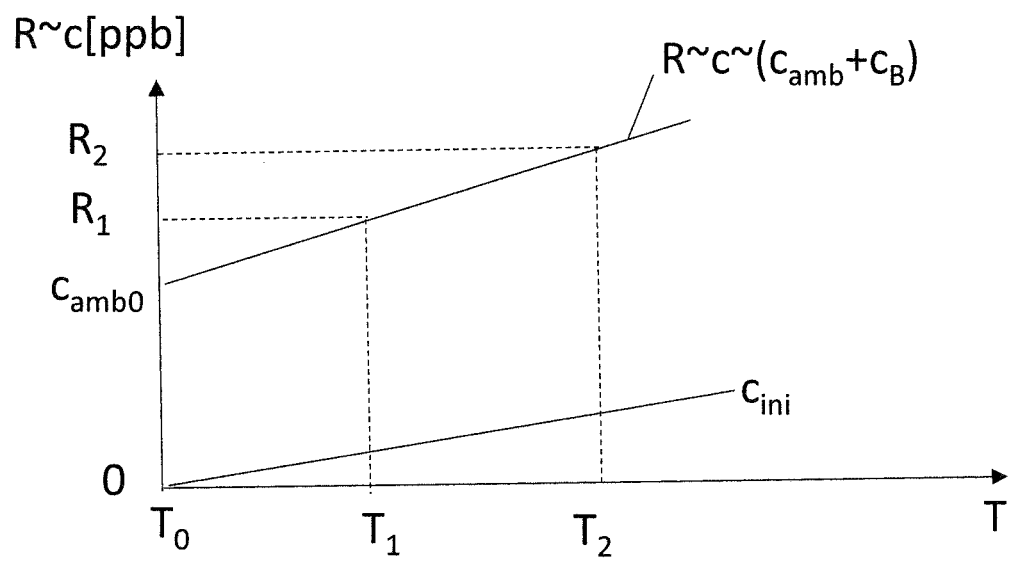

FIG. 3 illustrates a characteristic c(T) of the target gas concentration c over temperature T to be determined and quantified e.g. under the conditions for interval $0<t<t_1$ of FIG. 2. In particular, two first measurements are taken at two different temperatures $T_1$ and $T_2$, the results of which two first measurements are $R_1$ at temperature $T_1$, and $R_2$ at temperature $T_2$, having in mind that during the first measurements the environmental target gas concentration $c_{amb}=c_{amb0}$ is constant. Another assumption is that there is a temperature $T_0$, at which the device originating target gas concentration $c_B$ is or approximately is zero. For facilitating illustration, it is assumed that this temperature $T_0=0°$ C. Further, more realistically, the characteristic c(T) may follow a logarithmic function rather than a linear relation such that the characteristics and the corresponding equations rather include logarithmic or exponential functions. However, for the sake of illustration, the present linear function between c and T is assumed.

From the two measurement results $R_1$ and $R_2$ and the corresponding temperatures $T_1$ and $T_2$, a slope $\Delta R$ of the characteristic c(T) can be determined by:

$$\Delta R=(R_2-R_1)/(T_2-T_1) \quad \text{(II)}$$

On the other hand, the assumed present characteristic c(T) can be described by:

$$c(T)=c_{amb0}+\Delta R*T \quad \text{(III)}$$

such that in a next step the environmental target gas concentration $c_{amb0}$ present during the first measurements can be derived from (I) by means of:

$$c_{amb0}=c(T)-\Delta R*T \quad \text{(IV)}$$

and specifically by:

$$c_{amb0}=c(T_1)-\Delta R*T_1$$

wherein $c(T_1)=R_1$ such that finally the characteristic c over temperature T is described by:

$$c(T)=(R1-\Delta R*T1)+\Delta R*T \quad \text{(V)}$$

By means of equation (V), the device originating target gas concentration $c_B$ can be calculated by:

$$c_B(T)=c(T)-c_{amb0}=c(T)-(R1-\Delta R*T1) \quad \text{(VI)}$$

Hence, for any concentration $R \sim c$ measured during an operational measurement, in combination with knowing or measuring the corresponding temperature T, the corresponding device originating target gas concentration $c_B$ can be determined by equation (VI).

The lower graph in FIG. 3 referred to by $c_{ini}$ shows a characteristic that initially is used in the electronic device prior to the first determination of the (upper graph) characteristic c(T). Such initial characteristic may be measured and recorded in the device e.g. at the manufacturer of the gas sensor or the electronic device. In the present example, the subject one or more gas sensors may be located in a defined environment, e.g. a test/calibration environment where the environmental target gas concentration $c_{amb}$=0, or, alternatively is at a defined level known. The one or more electronic devices may be heated to different temperatures T and the measurement results may be processed to the characteristic $c_{ini}$(T) and recorded in the gas sensor or in the device. As can be derived from FIG. 3, the slope of the characteristic may change over time. Presently, c(T) has steeper rise than $c_{ini}$(T). In another embodiment, subsequent to the determination of c(T), either at fixed intervals or in response to a trigger, the characteristic c(T) may be updated into $c_{upd}$(T) by applying the same routines as during the first measurements PM described.

Returning to FIG. 2, once the device originating target gas concentration $c_B$(T) is determined—e.g. according to equation (VI) or any other equation that matches the subject characteristic—operational measurements OM can be conducted. The only difference of an operational measurement OM from a preparatory measurement PM is that for the operational measurement OM the device originating target gas concentration $c_B$ is to be determined upfront, and that, of course, the measurement conditions now allow for a varying environmental target gas concentration $c_{amb}$.

In FIG. 2, in the second interval $t_1 < t < t_2$, two operational measurements OM are conducted at times $t_{11}$ and $t_{12}$ resulting in two second measurement results $R_{OM}$. While at time $t_{11}$ the device is not heated and thus $c_B$ is not increased but remains constant at a constant value $c_{B0}$ for the subject temperature T, the environmental target gas concentration $c_{amb}$ rises, e.g. because the subject target gas concentration actually rises in the environment of the electronic device. At time $t_{12}$ instead, the rise of the environmental target gas concentration $c_{amb}$ has stopped at $c_{amb1}$, however, the device was heated again such the device originating target gas concentration $c_B$ exceeds $c_{B0}$.

Accordingly, and decoupled from any specific embodiment, the environmental target gas concentration $c_{amb}$ preferably is calculated by:

$$c_{amb} = \left(\frac{R_{OM}}{R_B}\right)^{\frac{1}{n}} * c_B - c_B \quad (VII)$$

wherein:
$c_B$ is the device originating target gas concentration for the subject temperature T, may be determined e.g. by equation (VI) with c(T)=$R_{OM}$; T may be measured by the temperature sensor;
$R_{OM}$ is the second measurement result, i.e. the raw data of the gas sensor measured at e.g. at $t_{11}$ or $t_{12}$;
$R_B$ is also referred to as baseline concentration, i.e. measurement result R corresponding to the device originating target gas concentration $c_B$ at the subject temperature T;
n is the sensitivity of the gas sensor.

Figure 4:
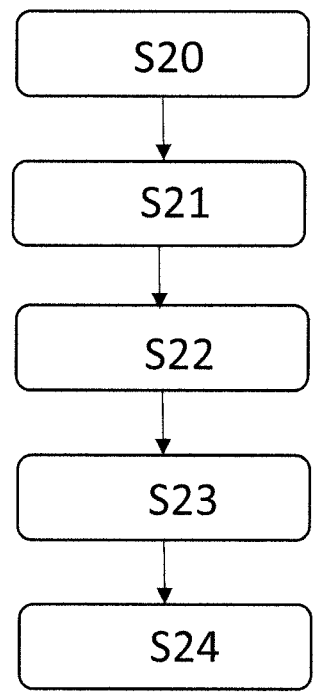

FIG. 4 illustrates a sample flow chart of a method according to an embodiment of the present invention, e.g. with reference to FIG. 2: In step S20, the gas sensor takes a measurement and returns $R_{OM}$ as a result. In step S21, the present temperature T($t_{11}$) is measured. In step S22, the device originating target gas concentration $c_B$ is looked up for the specific temperature T(t11). In step S23, the environment originating target gas concentration $c_{amb}$ is determined according Formula (VII).

In step S24, appropriate measures may be taken in response to the determination of the environmental target gas concentration $c_{amb}$, such as issuing a warning in case the environmental target gas concentration $c_{amb}$ exceeds a threshold, the threshold e.g. representing a toxic concentration level, or displaying the determined environmental target gas concentration $c_{amb}$ on a display of the electronic device, or transmitting the environmental target gas concentration $c_{amb}$ to a server or a different device for further processing.

As to the second operational measurement, the gas sensor provides a measured value $R_{OM}$ at t=$t_{12}$, while the same steps S20 to S24 are executed. The only difference is that a different device originating target gas concentration value $c_B$ is determined in view of a different temperature T measured at time t=$t_{12}$ compared to the temperature measured at time t=$t_{11}$.

While there are shown and described presently preferred embodiments of the invention, it is to be distinctly understood that the invention is not limited thereto but may be otherwise variously embodied and practised within the scope of the following claims.

The invention claimed is:

1. Method for determining a concentration of a target gas in an environment of an electronic device by means of a gas sensor sensitive to the target gas and arranged inside a housing of the electronic device or attached thereto, comprising
conducting one or more first measurements by the gas sensor resulting in one or more first measurement results,
determining a concentration of the target gas outgassed from one or more components of the housing or inside the housing dependent on the one or more first measurement results, wherein outgassing is understood as the release of chemical substances from the one or more components,
conducting a second measurement by the gas sensor resulting in a second measurement result, and
determining the environmental target gas concentration dependent on the determined outgassed target gas concentration and dependent on the second measurement result.

2. Method according to claim 1,
wherein the one or more first measurements are preparatory measurements conducted to determine the outgassed target gas concentration,
wherein the second measurement is an operational measurement conducted to determine the environmental target gas concentration, and
wherein the first and/or second measurement results depend on both the environmental target gas concentration and the outgassed target gas concentration.

3. Method according to claim 1, comprising
conducting the more first measurements at different temperatures of the electronic device, resulting in the first measurement results being temperature dependent.

4. Method according to claim 3, comprising
determining outgassed target gas concentrations for different temperatures dependent on the temperature dependent first measurement results.

5. Method according to claim 4, comprising
measuring a temperature in combination with each of the first measurements at a location of the gas sensor, and
storing each outgassed target gas concentration as determined in combination with the corresponding temperature as measured.

6. Method according to claim 3, comprising
determining a characteristic of outgassed target gas concentration over temperature from the temperature dependent first measurement results and the different temperatures by interpolation or by extrapolation.

7. Method according to claim 6, comprising
determining the characteristic from weighting the temperature dependent first measurement results.

8. Method according to claim 7, comprising
determining a slope of the characteristic from a difference between two of the first measurement results divided by a difference between the different temperatures associated with the two first measurement results,
determining an offset of the characteristic subject to the determined slope and subject to at least one of the two first measurement results and the different temperatures associated with the two first measurement results,
wherein the characteristic is determined subject to the determined slope and subject to the determined offset.

9. Method according to claim 3, comprising
measuring a temperature in combination with the second measurement at a location of the gas sensor, and
determining the environmental target gas concentration for the subject temperature dependent on the outgassed target gas concentration as determined for the measured temperature and dependent on the second measurement result,
wherein the outgassed target gas concentration for the subject temperature is determined from the characteristic by entering the temperature measured and one of calculating, looking up or determining the outgassed target gas concentration for this temperature.

10. Method according to claim 1, comprising
starting the first measurements in response to a trigger indicating varying temperatures to be expected and
in response to a change in the measured temperature at a location of the gas sensor.

11. Method according to claim 10, comprising
starting the first measurements in response to detecting a recharge process of a battery of the electronic device.

12. Method according to claim 1, according to claim 10, comprising
conducting the first measurements during a period in time in which the environmental target gas concentration is expected to be constant,
starting the first measurements at a predetermined point in time, wherein the predetermined point in time is defined as a specific time of day, at night, per one of days, multiple of days, weeks, multiple of weeks, months, or multiple of months.

13. Method according to claim 1, comprising
repeating the step of conducting the one or more first measurements by the gas sensor and resulting in one or more updated first measurement results,
determining an updated concentration of the target gas outgassed from the one or more components of the housing or inside the housing dependent on the one or more updated first measurement results, and
subsequent to the determination of the updated outgassed target gas concentration determining the concentration of the target gas in the environment of the electronic device dependent on the updated determined outgassed target gas concentration and dependent on the second measurement result.

14. Method according to claim 1, comprising
determining the environmental target gas concentration lamb according to:

$$c_{amb} = \left(\frac{R_{OM}}{R_B}\right)^{\frac{1}{n}} * c_B - c_B$$

wherein:
$c_B$ is the outgassed target gas concentration;
$R_{OM}$ is the second measurement result;
$R_B$ is the measurement result corresponding to the outgassed target gas concentration $c_B$;
n is the sensitivity of the gas sensor.

15. Method according to claim 1,
wherein the target gas includes a volatile organic compound.

16. Computer program element, comprising computer program code for performing the following steps when executed on a processing unit:
receiving one or more first measurement results taken by a gas sensor sensitive to a target gas and arranged in or at an electronic device,
determining a concentration of the target gas outgassed from one or more components of the housing or inside the housing dependent on the one or more first measurement results, wherein outgassing is understood as the release of chemical substances from the one or more components,
receiving a second measurement result taken by the gas sensor, and
determining a concentration of the target gas in an environment of the electronic device dependent on the determined outgassed target gas concentration and dependent on the second measurement result.

17. Electronic device, comprising
a gas sensor sensitive to a target gas and arranged inside a housing of the electronic device or attached thereto to detect a concentration of the target gas in an environment of the electronic device, and
a processing unit configured to
determine a concentration of the target gas outgassed from one or more components of the housing or inside the housing dependent on one or more first measurement results supplied by the gas sensor in response to one or more first measurements, wherein outgassing is understood as the release of chemical substances from the one or more components, and
determine the environmental target gas concentration dependent on the determined outgassed target gas concentration and dependent on a second measurement result supplied by the gas sensor in response to a second measurement.

18. Electronic device according to claim 17, comprising
a temperature sensor configured to measure a temperature at a location of the gas sensor.

19. Electronic device according to claim 18, wherein the housing comprises a cavity, wherein the gas sensor is arranged in or at the cavity, and wherein the temperature sensor is configured to measure a temperature inside the cavity.

* * * * *